US00PP37046P2

(12) United States Plant Patent
Hansen

(10) Patent No.: US PP37,046 P2
(45) Date of Patent: Oct. 21, 2025

(54) ***EUPHORBIA* PLANT NAMED 'Urge to Splurge'**

(50) Latin Name: ***Euphorbia epithymoides* L.**
Varietal Denomination: Urge to Splurge

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,570

(22) Filed: Apr. 25, 2025

(51) Int. Cl.
*A01H 5/02* (2018.01)
*A01H 6/38* (2018.01)

(52) U.S. Cl.
USPC ..... Plt./302
CPC ..... *A01H 6/38* (2018.05)

(58) Field of Classification Search
USPC ..... Plt./302
CPC ..... A01H 5/02
See application file for complete search history.

*Primary Examiner* — Kent L Bell

(57) ABSTRACT

A new and distinct cultivar of *Euphorbia* plant named 'Urge to Splurge' characterized by compact stems with obovate, bluish-green, glaucous foliage that develops a reddish tint in the summer and fall. The flowers are surrounded by bright yellow bracts and cover the plant in spring.

2 Drawing Sheets

Botanical classification: *Euphorbia epithymoides* L.
Cultivar denomination: 'Urge to Splurge'.

STATEMENT REGARDING PRIOR DISCLOSURES UNDER 37 CFR 1.77(B)(6)

The first offering of the new plant was on May 17, 2024, by Walters Gardens, Inc. to Dallas Johnson Greenhouse, Inc. On Dec. 1, 2024, the new plant was first listed on websites for Proven Winners Direct™ in the form of photographs and a brief description. Proven Winners Direct™ and Walters Gardens, Inc. both obtained the plant and all information relating thereto directly or indirectly from the inventor. No plants of *Euphorbia* 'Urge to Splurge' have been sold, in this country or anywhere in the world, nor has any disclosure of the new plant been made more than one year prior to the filing date of this application, and such sale or disclosure within one year was either derived directly or indirectly from the inventor and would therefore be a 35 U.S.C. § 102b exception.

BACKGROUND OF THE INVENTION

The present invention relates to the new and distinct cultivar of Cushion Spurge from the genus *Euphorbia* given the cultivar name 'Urge to Splurge'. The new plant was the result of an open pollination with 'Bonfire' U.S. Plant Pat. No. 18,585 as the female parent and the male parent was an unknown, non-introduced, proprietary individual seedling within a group of different *E. epithymoides* plants at a wholesale perennial nursery in Zeeland, Michigan in September of 2019. The new clone was first selected from trials at a wholesale perennial nursery in Zeeland, Michigan during the spring of 2021 as a single seedling clone and given the breeder code number 19-1-3 later in the evaluation processes.

*Euphorbia* 'Urge to Splurge' has been asexually propagated at the same nursery in Zeeland, MI since 2021 using traditional shoot tip cutting procedures and found to reproduce plants that are identical and exhibit all the characteristics of the original plant in successive generations.

SUMMARY OF THE INVENTION

Plants of the new cultivar have not been observed under all possible combinations of environmental conditions and cultural practices. The phenotype may vary with variations in the environment including growing temperature, available sunlight, nutrition, water, etc. without a change in the genotype of the plant.

*Euphorbia* 'Urge to Splurge' is unique from all other Cushion Spurge known to the inventor. Several other cultivars may have some similar traits, but this is the only variety known by the inventor to have the following characteristic combinations that establish the new plant as unique:

1. Compact, stems with oblanceolate, bluish-green, glaucous foliage in spring that develops a reddish tint in the summer and fall;
2. Good flower coverage;
3. Flowering in short cyathia with bright yellow flowers surrounded by bright yellow bracts;
4. Maintains foliage through the season with good disease and browsing resistance.

The closest comparison plants to the new plant known to the inventor include: 'Candy' (not patented), 'First Blush' U.S. Plant Pat. No. 15,292. 'Bonfire' U.S. Plant Pat. No. 18,585 is slightly more compact and shows foliage and floral bracts with more intense reddish purple with orangish tint coloration earlier in the summer and become more solid reddish earlier in the fall. 'Candy' has a shorter habit, with purple tinged foliage tips in early spring and has rosy-reddish foliage in the autumn. 'First Blush' has a more compact habit and light green foliage with white to rosy-colored leaf margins and rosy flower bract margins surrounding the bright yellow flowers.

The specific male parent is unknown, but compared with the different plants within the group of *E. epithymoides* plants, the new plant has uniform glaucous foliage with a reddish tint in summer and fall, and compact habit.

BRIEF DESCRIPTION OF THE DRAWINGS

The drawings of 'Urge to Splurge' are of two-year-old plants grown in full-sun trial garden in Zeeland, Michigan showing the overall appearance of the plant including the unique traits. The colors are as accurate as reasonably possible with color reproductions. Some slight variation of color may occur as a result of lighting quality, intensity, wavelength, direction or reflection.

DETAILED BOTANICAL DESCRIPTION

Figure 1:
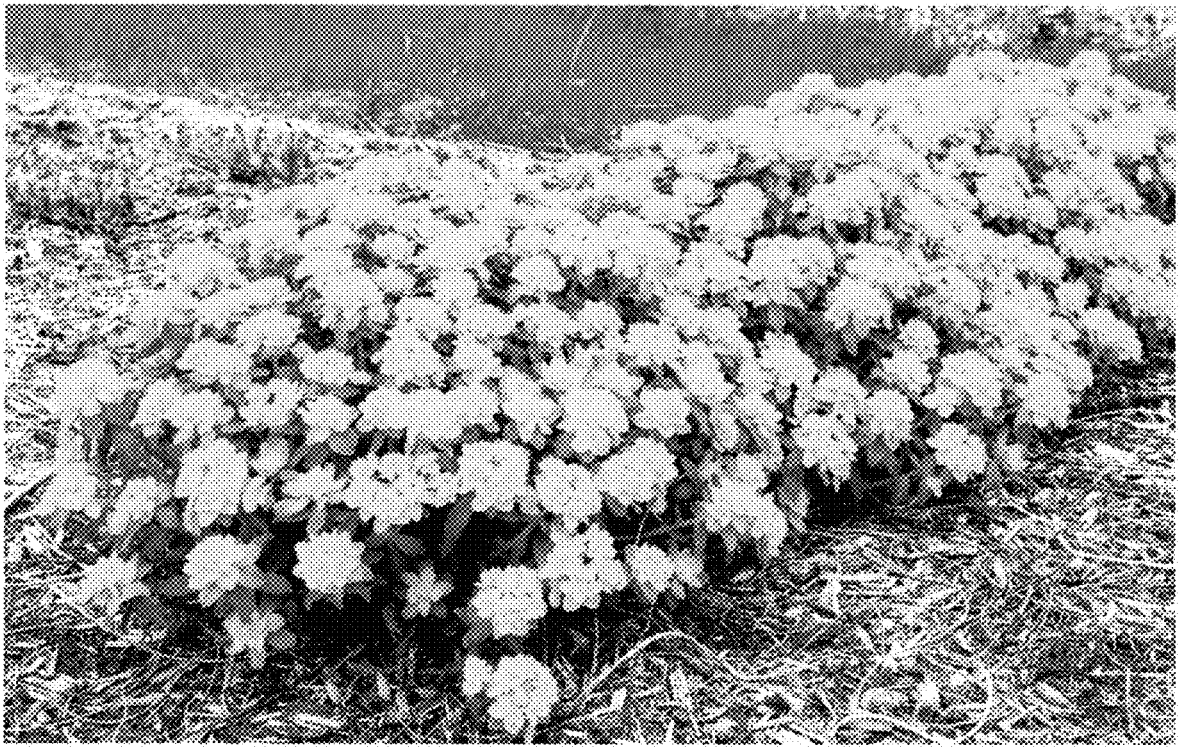
FIG. 1 shows the habit of three of the new plants in early-season flowering.
Figure 2:
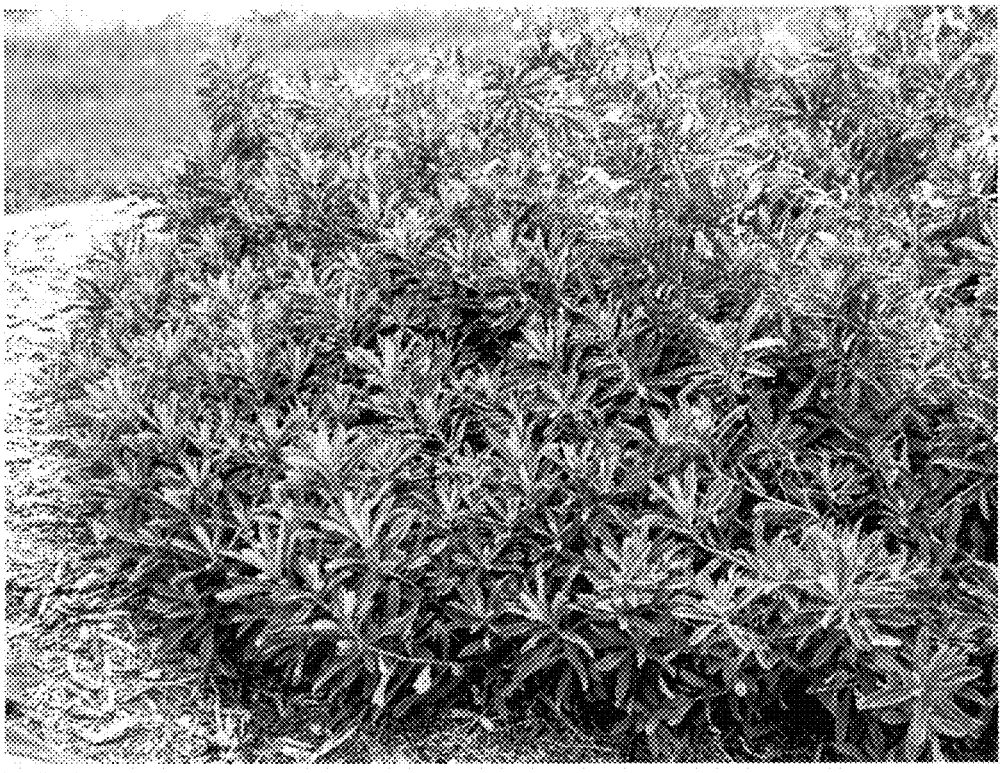
FIG. 2 shows the foliage of the new plant in early summer.
Figure 3:
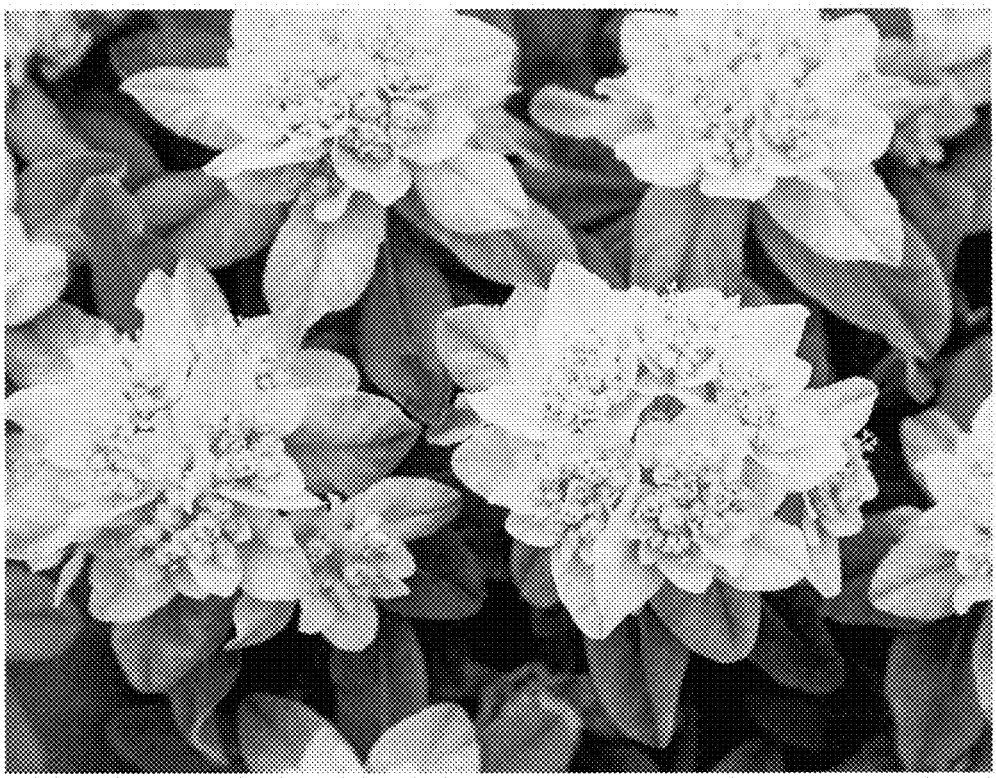
FIG. 3 shows a close-up of the flowers and buds.

The following detailed description of 'Urge to Splurge' is based on observations of two-year-old plants in a full-sun trial garden at a nursery in Zeeland, MI with supplemental watering, light additions of fertilizer, and free of other plant growth regulators. All color usage is in accordance with the 2015 edition of The Royal Horticultural Colour Chart except where common dictionary terms are used.

Parentage: The female or seed parent is 'Bonfire'; the male or pollen parent is an unknown, non-introduced, proprietary;

Plant habit: Herbaceous, deciduous, winter-hardy perennial; early spring flowering on compact mounds; developing taller stems after flowering;

Plant size: Flowering to about 20 cm and about 30 cm across; foliage developing to about 62 cm tall and about 120 cm wide;

Root system: Fine, fibrous; freely branching; color nearest RHS 155D depending on soil substrate, composition, and nutrition;

Vigor: Moderately vigorous; spring planted plugs finish in 3.8-liter pots in eight to ten weeks;

Propagation: Terminal vegetative cuttings.

Time to initiate roots: About 20 days;

Growth rate: Moderate to rapid; finishing to flower in a 3.8-liter pot in 13 weeks;

Stems: Main stems cylindrical; puberulent distally, glabrate proximally; to about 43 cm long and 7 mm diameter near base; highly branched;

Branches: Cylindrical; puberulent distally, glabrate proximally; freely branching habit; to about nine lateral branches develop on the distal stem; to about 42 cm long and 2 mm diameter; aspect mostly outward;

Internode length: Average about 0.5 cm; longer proximally and shorter distally;

Node color: Distal portion nearest RHS 146D; proximal portion between RHS 183D and RHS 182C;

Strength: Moderately strong, flexible;

Branch color: Distal portion nearest RHS 146D; proximal portion between RHS 183D and RHS 182C;

Leaves: Oblanceolate; alternate; simple; apex rounded to bluntly acute; base sessile, attenuate; margin entire, ciliolate; adaxial puberulent and abaxial micro-puberulent, matte; to about 5 cm long and 1.2 cm wide;

Leaf color: Young expanding adaxial between RHS 146A and RHS 146B with a thin margin less than 0.3 mm between RHS 187A and RHS 187B, young expanding abaxial nearest RHS 146B with a light to moderate blush of between RHS 187A and RHS 187B; mature adaxial nearest RHS NN137A, mature abaxial between RHS NN137B and RHS 187A;

Veins: Pinnate, reticulate; glabrous and flat adaxial; weakly costate and glabrous abaxial, abaxial midrib glaucous;

Vein color: Young expanding adaxial midrib nearest RHS 185C, pinnate veins between RHS 146A and RHS 146B, young expanding abaxial midrib nearest RHS 181C and pinnate veins nearest RHS 181A; mature adaxial midrib proximal half nearest RHS 182B, midrib becoming nearest RHS 185C in the central portion, and distal midrib and pinnate veins nearest RHS 147C; mature abaxial midrib between RSH 182B and RHS 182C with the pinnate veins between RHS 187A and RHS 137A;

Petioles: Sessile;

Inflorescence: With about 300 to 600 cyathia in corymb-like raceme and up to 8 main branches having up to 30 cyathia per main branch; with numerous bracts subtending cyathia branches and whole inflorescence; aspect upright and outwardly, produced above the foliage; about 250 inflorescences per plant;

Inflorescence size: Compound branched to about 4.4 cm diameter and to about 2.8 cm tall;

Bud: Ellipsoid; about 2 mm tall and 1.5 mm diameter;

Bud color: Nearest RHS 1C;

Flower: Cyathium; perfect; incomplete; to about 5 mm long to exerted anthers and about 3 mm wide;

Reproductive organs:

*Gynoecium*.—Single pistil; to about 2 mm long; on cylindrical pedicel about 0.5 mm long and 0.3 mm diameter; pedicel color nearest RHS 145B.

*Style*.—Short to about 1 mm long and 0.3 mm diameter; color nearest RHS 145B.

*Stigma*.—Trifid; about 1 mm long; color nearest RHS 145B.

*Ovary*.—Globose; about 1 mm diameter; color nearest RHS 145B.

*Androecium*.—Five.

*Filament*.—Cylindrical; glabrous; about 4 mm long and 0.3 mm diameter; color nearest RHS 145D.

*Anther*.—Bi-lobed; about 1 mm long and 0.5 mm across; color nearest 12A.

*Pollen*.—Abundant; color nearest RHS 13A.

Glands: Five; outside filaments; globose; about 1 mm diameter; color nearest RHS 145B;

Fruit and seed: Not yet observed;

Flower fragrance: None detected;

Flowering season: Plants typically flower during the late spring to early summer in the Northern Hemisphere; lasting about three to four weeks on the plant;

Flower aspect: Mostly upright;

Flower size: To about 1.8 cm diameter and about 7.5 mm tall;

Floral bracts: About 350 to 400 per inflorescence; typically, one subtending each main, secondary, and tertiary branch; proximal bracts lanceolate, acute apices, truncate bases, entire ciliolate margins, puberulent adaxial and abaxial; distal secondary and tertiary bracts distally becoming more ovate, nearly rounded apices, truncate bases, entire ciliolate margins, micro-puberulent adaxial and puberulent abaxial; proximal bracts to about 3.3 cm long and 1.4 mm wide; distal bracts decreasing distally from about 2.6 cm long and 1.2 cm wide to 5 mm long and 3 mm wide; involucre cup-shaped;

Floral bract color: Proximal bracts adaxial in distal portion between RHS 146B and RHS 146C and proximal portion between RHS N144B and RHS N144D, abaxial distal portion between RHS N187A and RHS N186C with an undertone of nearest RHS 138A and proximal portion between RHS N144B and RHS N144D; distal most bracts between RHS 151C and RHS 1A both adaxial and abaxial; intermediate bracts adaxial proximal portion nearest RHS 154B, distal portion between RHS 151A and RHS 151B with a faint blush of nearest RHS N186C, abaxial proximal portion nearest RHS 154B and distal portion variable with RHS 151A and mottled lightly with nearest RHS 187C;

Floral bract veins: Adaxial glabrous, proximal bracts puberulent abaxial and glabrous on distal bracts;

Floral bract vein color: Proximal bracts adaxial midrib nearest RHS 193B with moderate blush of between RHS 185B and RHS 185C, distal bracts between RHS N144B and RHS N144D both adaxial and abaxial;

Pedicel: Cylindrical; glabrous; to about 4 mm long and 0.7 mm diameter; aspect erect; flexible;

Pedicel color: Nearest 145B.

Pathogen and pest resistance: The new *Euphorbia* has not been shown to be resistant or susceptible to pathogens and pests common to *Euphorbia* plants.

Winter hardiness: The new *Euphorbia* is able to withstand conditions in USDA zones 4 to 9.

I claim:

1. A new and distinct *Euphorbia* Plant named 'Urge to Splurge' as herein illustrated and described.

* * * * *